United States Patent [19]

Bailey et al.

[11] Patent Number: 4,728,598
[45] Date of Patent: Mar. 1, 1988

[54] PHOTOGRAPHIC COLOR COUPLERS, PHOTOGRAPHIC MATERIALS CONTAINING THEM AND METHOD OF FORMING DYE IMAGES

[75] Inventors: Joseph Bailey, Bushey Heath; David N. Rogers, Harrow, both of United Kingdom

[73] Assignee: Eastman Kodak Company, Rochester, N.Y.

[21] Appl. No.: 858,147

[22] PCT Filed: Oct. 14, 1985

[86] PCT No.: PCT/GB85/00460
§ 371 Date: May 1, 1986
§ 102(e) Date: May 1, 1986

[87] PCT Pub. No.: WO86/02467
PCT Pub. Date: Apr. 24, 1986

[30] Foreign Application Priority Data

Oct. 19, 1984 [GB] United Kingdom ............... 8426447

[51] Int. Cl.$^4$ .................... G03C 1/40; G03C 7/38
[52] U.S. Cl. ................... 430/387; 430/386; 430/544; 430/548; 430/551; 430/558
[58] Field of Search .......... 430/558, 551, 386, 387, 430/544, 548, 384, 385

[56] References Cited

FOREIGN PATENT DOCUMENTS 119741 9/1984 European Pat. Off. .

OTHER PUBLICATIONS

Research Disclosure, Sep. 1974, Item No. 24531, pp. 442–454.
"The Theory of the Photographic Process", edited by T. H. James, Macmillan, N.Y., N.Y., p. 358 (1977).
"The Photographic Color Development Process" by Bailey and Williams in *Chemistry of Synthetic Dyes*, edited by K. Venkataraman, Academic Press Inc., N.Y. and London, vol. 4, p. 341 (1971).
Research Disclosure, Oct. 1977, Item No. 16216, pp. 73–76.
Research Disclosure, Dec. 1978, Item No. 17643, pp. 22–31.
Research Disclosure, Jun. 1984, Item No. 24220, pp. 253–258.

Primary Examiner—Richard L. Schilling
Attorney, Agent, or Firm—Richard E. Knapp

[57] ABSTRACT

Novel photographic dye-forming couplers comprise an imidazo[1,2-b]pyrazole nucleus which reacts at its 3-position with an oxidized aromatic primary amino color developing agent. These couplers are monomeric or polymeric and are useful in photographic materials and processes and have improved absorption and solubility characteristics.

9 Claims, No Drawings

PHOTOGRAPHIC COLOR COUPLERS, PHOTOGRAPHIC MATERIALS CONTAINING THEM AND METHOD OF FORMING DYE IMAGES

This invention relates to a new class of photographic color couplers comprising an imidazo[1,2-b]pyrazole nucleus, to photographic materials containing them and to a method of forming a dye image in such photographic materials.

A number of nitrogen-containing heterocyclic compounds have been proposed for color couplers. Pyrazolone couplers, for example, are widely used as maganta dye-forming couplers. Other couplers are described in Bailey and Williams, "The Photographic Color Development Process" in the Chemistry of Synthetic Dyes, ed. K. Venkataraman, Academic Press, Inc., New York and London, Volume 4, 341 (1971). Further couplers are the pyrazolo[3,2-c]-s-triazoles and imidazo[1,2-b]-s-triazoles described in The Theory of the Photographic Process, ed. T. H. James, Macmillan, New York, page 358 (1977) and Research Disclosure No. 16216, 1977, 73–75 respectively.

Research Disclosure 24531 (September 1984) published by Industrial Opportunities Ltd., The Old Harbourmaster's, 8 North Street, Emsworth, Hants PO10 7DD, U.K. contains, inter alia, a reference to couplers of the general formula:

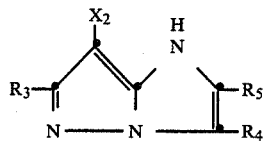

wherein $X_2$ is hydrogen or a coupling-off substituent while $R_3$, $R_4$ and $R_5$ are hydrogen or one of a number of specified substituents. Structural formulae of specific couplers within this general formula are listed but no examples of their preparation or use are given.

The present invention provides novel dye-forming color couplers.

According to the present invention there is provided a photographic color coupler which comprises an imidazo[1,2-b]pyrazole nucleus and which reacts at its 3-position with an oxidized aromatic primary amino color developing agent.

Preferred couplers have the general formula:

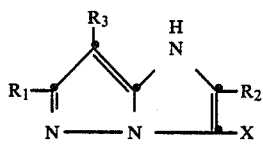

(I)

in which $R_1$ and $R_2$ are each hydrogen or a substituted or unsubstituted alkyl, a substituted or unsubstituted aryl, substituted or unsubstituted heterocyclic, hydroxy, nitrile, sulfone, acylamido, sulfonamide, sulfamoyl, alkoxycarbonyl, aryloxycarbonyl or nitro group, an amino or substituted amino group, a carbamoyl or substituted carbamoyl group, a non-coupling-off alkoxy group or a non-coupling-off phenolic stabilizer moiety, $R_3$ is any of the non-coupling-off groups which $R_1$ and $R_2$ may represent and is not hydrogen, and X is hydrogen or a group which splits off during coupling;

and in which one of the substituents $R_1$, $R_2$ or $R_3$ optionally contains an ethylenically unsaturated polymerisable group.

It is known that pyrazolotriazole (PTs) and pyrazolobenzimidazole (PBIs) dyes have better absorption characteristics (viz. less blue absorption) than the corresponding pyrazolone dyes. The dyes from the couplers of the present invention also have good absorption properties, and since they have only two fused rings compared with the PBIs which have three, they have, in consequence, better solubility and thus are easier than PBIs to disperse in photographic emulsions. Furthermore, the couplers of the present invention in comparison with PT couplers have one extra site to carry an additional substittuent. This extra substituent can be used through electronic and steric effects to finely control parameters such as $pK_a$ and reactivity. Hence higher activity couplers can be obtained from this new series of compounds. The absorption $\lambda$max can also be varied; the examples below show $\lambda$max variations from 529–620 nm.

Examples of substituents $R_1$, $R_2$ and $R_3$ include alkyl radicals which may have a straight or branched chain and may be substituted and preferably contain 1–22 carbon atoms, e.g. methyl, ethyl, n-propyl, isopropyl, sec-butyl, tert-pentyl, n-hexyl or 2-aminoethyl; aryl radicals which may be substituted, e.g. phenyl, 4-methylphenyl; heterocyclic radicals e.g. pyridyl or thienyl; amino, methylamino, diethylamino, phenylamino; acylamido radicals e.g. ethylcarbonamido, n-decylcarbonamido, phenylethylcarbonamido, phenylcarbonamido; non-coupling alkoxy group or a non-coupling phenolic stabilizer moiety, e.g., as described in U.S. Pat. No. 3,519,429 (equivalent U.K. Specification No. 1,183,515). It is preferred that $R_3$ represents a substituent which cannot be replaced by oxidized color developing agent, that is, not a coupling-off group.

Examples of radicals which X may represent which split off during color development include:
a halogen atom, e.g. F, Cl, Br or I;
—SO$_3$H;
—COOH;
$R_4$-O or $R_4$-S- wherein $R_4$ is an alkyl, aryl or heterocyclic radical which may bear substituents e.g. phenyl, tolyl, tetrazolyl;
amino or substituted amino, e.g. methylamino, diethylamino or phenylamino, or any of the substituted amino groups described in British Specification No. 1,520,551;
acyloxy;
sulfonyloxy; or
heterocyclic, for example hydantoin, imidazopyrazoles, pyrazolo-triazoles, imidazo-s-triazoles, a phthalimido or benzotriazole.

Further groups that X may represent are the radicals of a photographically useful compound which compound is released on coupling. Examples of such compounds include development inhibitors, development accelerators, developing agents, electron transfer agents, color couplers and azo dyes. Examples of such X groups include:

—S—alkylene-COOH

-continued

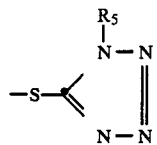

wherein $R_5$ is aromatic, heteroaromatic, or alkyl, e.g. phenyl, ethyl, t-butyl or pyridyl.

In some applications $R_5$ may be a ballasting group which would render the coupler, and after coupling, the coupling-off group, nondiffusible. The alkylene group may be straight chain or branched and, again, could be a ballasting group.

Alternatively the radical of the photographically useful compound (PUC) may be linked via a group which aids the release of the compound by means of anchimeric assistance. An example of such a group is:

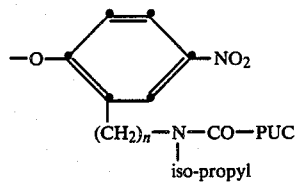

Other similar groups are described in British Patent Specification No. 2,010,818.

If the present couplers are to be incorporated into a photosensitive photographic material, they will normally contain a ballast group to render them nondiffusible. Examples of such ballast groups include alkyl groups of 8–22 carbon atoms. The ballast may be attached directly or indirectly in the 2, 6 or 7-position in formula (I).

A preferred class of the present couplers have the formula:

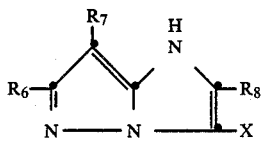

wherein $R_6$ is a substituted or unsubstituted alkyl group of 1–22 carbon atoms, $R_7$ is a substituted or unsubstituted alkyl or alkylcarbamoyl group in which the alkyl group has 1–22 carbon atoms, and $R_8$ is hydrogen or an alkyl or aryl group either of which is substituted or unsubstituted, and X is as defined above.

Another preferred class of color couplers comprise an imidazo[1,2-b]pyrazole nucleus which reacts at its 3-position with an oxidized aromatic primary amino color developing agent and which contains an ethylenically unsaturated polymerizable group. A preferred group of such color couplers have the general formula (I) above and contain a substituent comprising a polymerizable ethylenically unsaturated group. Such a group may be attached directly or indirectly to the fused ring nucleus of the coupler.

Such couplers have the general formula:

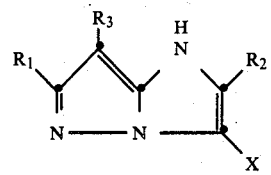

in which $R_1$ and $R_2$ are each hydrogen or a substituted or unsubstituted alkyl, a substituted or unsubstituted aryl, a substituted or unsubstituted heterocyclic, hydroxy, nitrile, sulfone, acylamido, sulfonamide, sulfamoyl, alkoxycarbonyl, aryloxycarbonyl or nitro group, an amino or substituted amino group, a carbamoyl or substituted carbamoyl group, a non-coupling-off alkoxy group or a non-coupling-off phenolic stabilizer moiety.

$R_3$ is any of the non-coupling-off groups which $R_1$ and $R_2$ may represent and is not hydrogen, and X is hydrogen or a group which splits off during coupling, and in which one of the substituents $R_1$, $R_2$ or $R_3$ contains an ethylenically unsaturated polymerizable group.

When indirectly linked the polymerizable group is attached via a linking group which may contain alkyl or aryl moieties, groups of the formula —O—, —S—, —CO—, —SO$_2$—, —NH—, —NHCO—, —NHSO$_2$—, —CONH— and —SO$_2$NH— or any combination thereof.

In particular the polymerizable couplers may be of general formula (I) in which $R_1$ or $R_2$ has the formula:

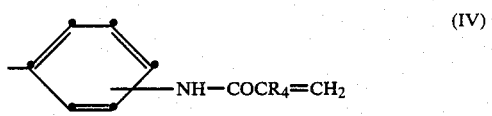

or in which $R_3$ has the formula:

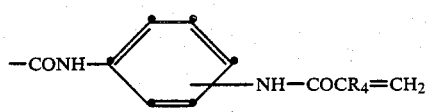

wherein $R_4$ is hydrogen or methyl.

The present couplers, especially those without polymerisable groups, may be prepared using the following routes:

Scheme 1

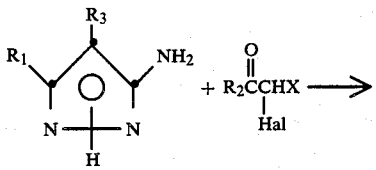

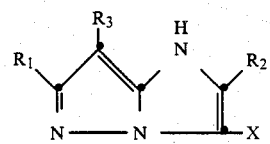

An alternative method of obtaining couplers of formula I wherein $R_3$ is —CN is:

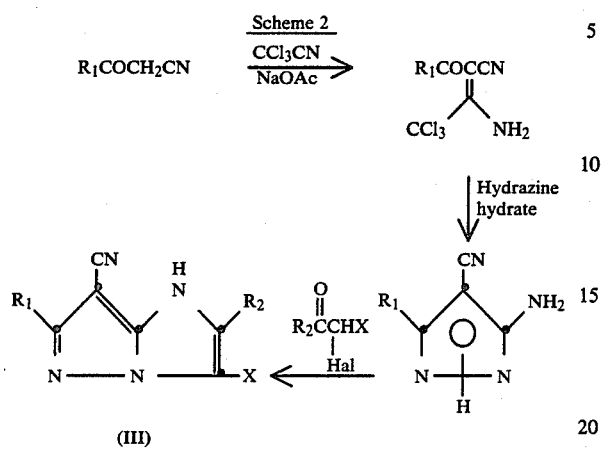

(III)

Coupler (III) may also be used to prepare amides containing a ballast group via an intermediate aldimine thus:

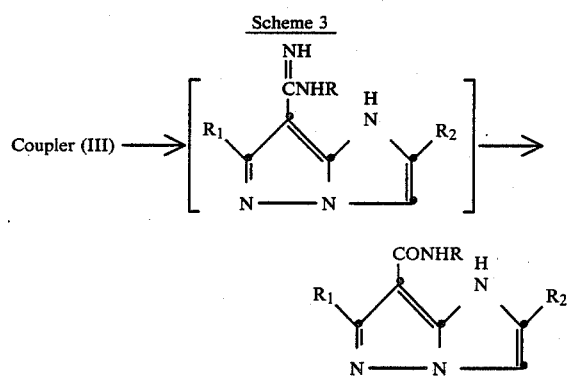

The method of preparation described above allow the present couplers to be prepared efficiently in the minimum number of steps and in good yields.

The polymerisable couplers may be prepared by one of the following reaction schemes:

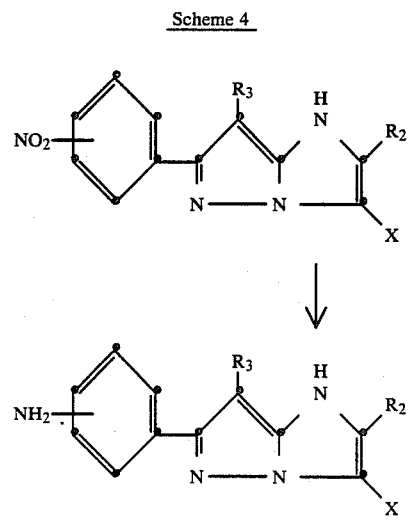

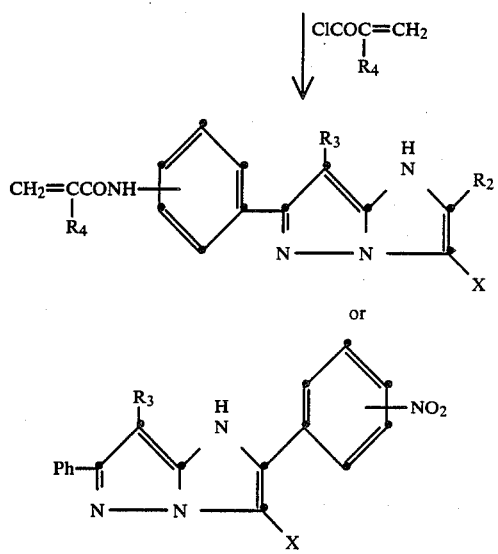

Using the starting compound, the procedure is analogous to Scheme 1.

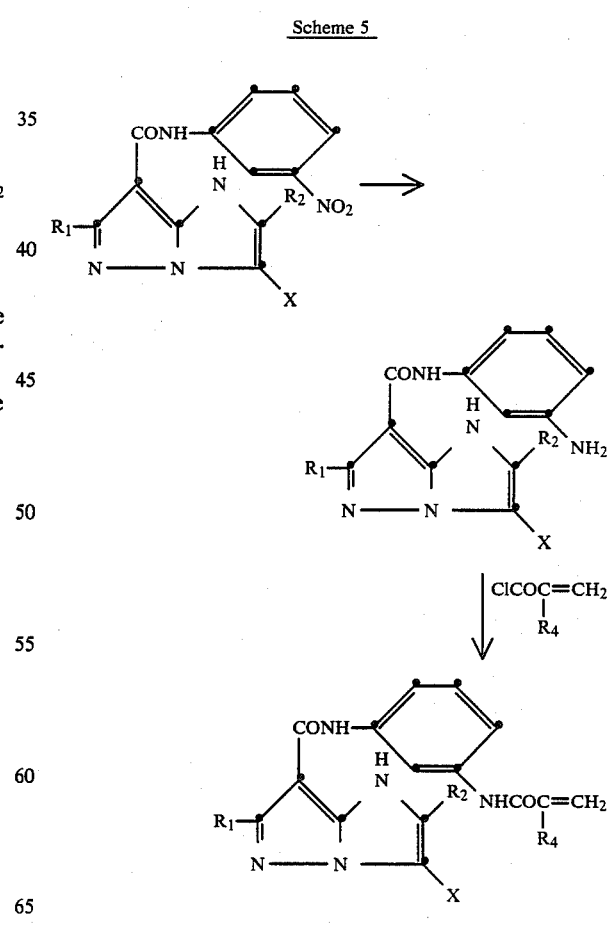

The following Table I lists specific examples of couplers according to Formula I.

TABLE I
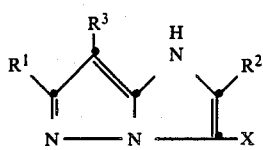
| Coupler No. | X | R¹ | R² | R³ |
|---|---|---|---|---|
| 1 | —H | —tBu | —Me | —CN |
| 2 | —H | -C₆H₄-NO₂ | —tBu | —CO₂Et |
| 3 | —H | —H | —tBu | —CN |
| 4 | —H | —H | —tBu | —CONH₂ |
| 5 | —H | —H | —tBu | —CO₂Et |
| 6 | —OPh | -C₆H₄-NO₂ | —tBu | —CO₂Et |
| 7 | —H | -C₆H₄-NH₂ | —tBu | —CO—Et |
| 8 | —H | -C₆H₄-NHCOCH(C₁₂H₂₅)-O-C₆H₄-NHSO₂ⁿBu | —tBu | —CO₂Et |
| 9 | —Cl | -C₆H₄-NO₂ | —tBu | —CO₂Et |
| 10 | —H | -C₆H₄-NO₂ | —Me | —CO₂Et |
| 11 | —H | -C₆H₄-NO₂ | —Ph | —CO₂Et |
| 12 | —H | —Ph | -C₆H₄-NO₂ | —CO₂Et |
| 13 | —OPh | -C₆H₄-NHSO₂C₁₆H₃₃ | —Me | —CN |
| 14 | —OPh | —Ph | —NHCOC₁₆H₃₃ | —CN |
| 15 | —Cl | —NHPh | —NHPh | -C₆H₃(Cl)(NHSO₂C₁₃H₂₇) |

TABLE I-continued

Structure (header): R¹, R³ on pyrazole ring; H-N; R², X (general coupler structure shown above table)

| Coupler No. | X | R¹ | R² | R³ |
|---|---|---|---|---|
| 16 | benzotriazolyl | 4-[NHCO-CH($C_{10}H_{21}$)-O-(phenyl)-$SO_2$-(phenyl)-OH]phenyl | —Me | —CN |
| 17 | —N=N—(3,4-dimethoxyphenyl) | 4-[CONH—CH($C_{12}H_{25}$)—O-(phenyl)-$NHSO_2^nBu$]phenyl | —Me | —Me |
| 18 | —O—CH$_2$—N($^iPr$)—CO—S—(1-phenyltetrazol-5-yl), with $CO_2H$ on phenyl | 2-chloro-5-($NHSO_2C_{14}H_{29}$)phenyl | —Me | —CN |

$t_{Bu}$ herein is tertiary-butyl.
Me herein is methyl.
Et herein is ethyl.
Ph herein is phenyl.

A specific preparation is as follows:

Scheme 6

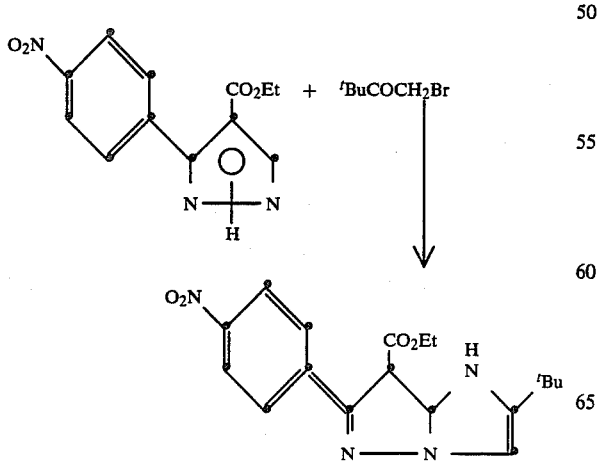

Substituent X (the leaving group in 2-equivalent couplers) may be introduced into the appropriate intermediate or added to the preformed imidazo[1,2-b]pyrazole viz. for incorporation during ring formation:

Scheme 7

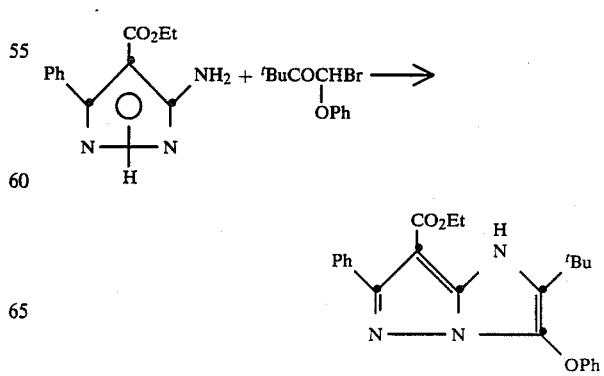

or for incorporation on the preformed coupler:

Scheme 8

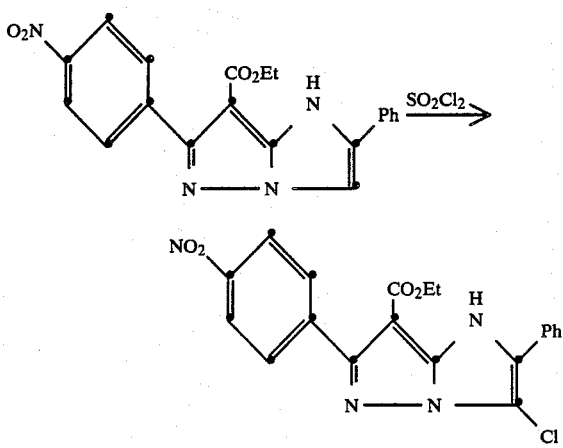

The present polymerizable compounds may be polymerized alone or with one or more comonomers to form a polymeric color coupler. The present invention also provides such couplers.

A preferred polymeric color coupler of the present invention has the formula:

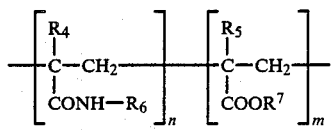

(VI)

wherein $R_5$ is hydrogen or methyl,
$R_7$ is alkyl of 1-5 carbon atoms which may be substituted,
$R_8$ is the radical of a coupler of formula (Ia),
n is 50-100%, and
m is 0-50%.

Preferred comonomer units are derived from ethylacrylate, butylacrylate and/or ethoxyethyl acrylate.

The dye-forming couplers of this invention can be used in the ways and for the purposes that dye-forming couplers have been previously used in the photographic art. They may be dissolved in processing solutions (unballasted) or incorporated into photographic materials (normally ballasted).

Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized color developing agent. Thus, as used herein, the term "associated therewith" signifies that the coupler is in the silver halide emulsion layer or in an adjacent location where, during processing, it will come into reactive association with silver halide development products.

The photographic elements can be a single color elements or multicolor elements. In a multi- this invention would usually be associated with a green-sensitive emulsion, although they could be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image forming units, can be arranged in various orders as known in the art.

A typical multicolor photographic element would comprise a support bearing a cyan dye image-forming unit comprised of at least one red-sensitive silver halide emulsion layer having associated therewith at least one magenta dye-forming coupler, at least one of the magenta dye-forming couplers being a coupler of this invention, and a yellow dye image-forming unit comprising at least one blue-sensitive silver halide emulsion layer having associated therewith at least one yellow dye-forming coupler. The element can contain additional layers, such as filter layers.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants PO10 7DD, U.K., the disclosures of which are incorporated herein by reference. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-N,N-diethylaniline hydrochloride, 4-amino-3-methyl-N-ethyl-N-β-(methanesulfonamido)ethylaniline sulphate hydrate, 4-amino-3-methyl-N-ethyl-N-β-hydroxyethylaniline sulphate, 4-amino-3-β-(methanesulfonamido)ethyl-N,N-diethylaniline hydrochloride and 4-amino-N-ethyl-N-(2-methoxyethyl)-m-toluidine di-p-toluene sulfonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

In assessing the usefulness of the present couplers, a number of properties can be determined.

The wavelength of maximum absorption of a dye solution ($\lambda$max) and the half bandwidth (HBW) can be determined by well known procedures.

For the purposes of determining $pK_a$ it is assumed that the coupler C—H, where C is the radical of the coupler is ionized, thus:

$$K_a = \frac{[C^-][H^+]}{[CH]}$$

and $pK_a$ is minus $\log_{10} K_a$.

In determining solution activity, measurements are taken of the rate at which coupler is consumed under specified test conditions:

$$\frac{d[C]}{dt} = k_c - [C^-][D_{ox}]$$

where $[D_{ox}]$ is the concentration of oxidized color developer. Alternatively:

$$\frac{d[C]}{dt} = k_c - \alpha[C][D_{ox}]$$

whence it can be seen that $$\alpha = \frac{[C^-]}{[C]}.$$

In Table II below, the values of $pK_a$, $\log K_c$ and $\log K_c\text{-}\alpha$ are given.

The following examples are included for a better understanding of the invention.

EXAMPLE 1

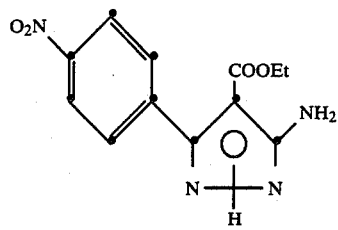

(Coupler 2)

Following the method of scheme 1 above, the compound of the formula:

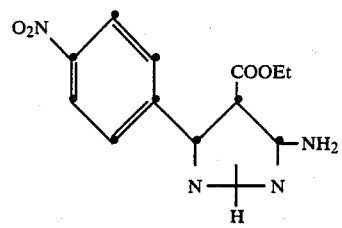

(8.1 g; 0.03 moles) was mixed with bromopinacolone (5.2 g; 0.06 moles), tetramethylguanidine (3.24 g; 0.03 moles) and acetonitrile (162 ml). The mixture was heated to reflux and maintained at that temperature for 20 hours. Solvent removal and column chromatography [silica; ethyl acetate (75%)/petrol 60–80 (25%)] afforded the desired product as a yellow solid; 81% yield, mpt. 187°–188° C.

|  | C | H | N |
| --- | --- | --- | --- |
| Found | 59.3 | 5.8 | 15.4 |
| Requires+ | 59.2 | 5.5 | 15.3 |

+Analysis for 0.5 M water of crystallization

3-Aminopyrazoles may be obtained from one of several general methods which are outlined in the following references: (1) L. C. Behr, F. Fusco and C. H. Jarboe "Pyrazoles, pyrazolines, pyrazolidines, indazoles and condensed rings", ed. R. H. Wiley, Interscience, New York, 1967; (2) M. H. Elnagdi et al, J. Heterocycl. Chem. 1979, 16, 1109; (3) R. Gompper and W. Töpft, Chem. Ber., 1962, 95, 2861, 2871, 2877.

α-Haloketones are described throughout the literature, however several general texts contain references to their preparation. Amongst these general texts are: (1) R. D. Chambers and S. R. James in "Comprehensive Organic Chemistry," ed. DHR Barton and W. D. Ollis, Pergamon Press, Oxford, 1979, vol. 1, p. 491; (2) M. and L. F. Fieser in "Reagents for Organic Synthesis", Wiley, New York, 1974, vol. 4, p. 138; (3) "The Chemistry of the Carbon-Halogen Bond, part 2", ed. S. Patai, Wiley, New York, 1973; (4) "Organic Reactions", ed. R. Adams et al, Wiley, New York, 1947, 4th printing, vol. 1, p. 1; (5) "Organic Reactions", ed. J. Baldwin et al, Wiley, New York, 1975, p. 423.

EXAMPLE 2

A number of other compounds are prepared by the method of Example 1 except for Couplers (1) and (3) in which the pyrazole was obtained by the method shown in scheme (2). The λmax EtOAc, and half-band width are given for the derived dye, where the developer moiety is that derived from the developer 4-N-ethyl-N-(β-methanesulfonamidoethyl)amino-o-toluidine sesquisulfate (CD3).

Solution activity parameters log $k_{c}$-α and log $k_{c}$- at pH 10 and 20° C. and pKa measurements were also recorded for representative imidazo[1,2-b]pyrazoles. Solution activity was measured using the stop-flow method of Tong [e.g. L. K. J. Tong, J. Phys. Chem., 1954, 58, 1090-97 (Comm. 1649)]. The contents of the two input syringes were:

| Solution A | |
|---|---|
| Color developing agent CD3 | $1 \times 10^{-3}$ mol. |
| Coupler (0.1% ethanolic solution) | 10 ml. |
| Solvent buffer* | 1 l |
| pH adjusted with H₂SO₄ or NaOH | to pH 10 |
| Solution B | |
| Potassium ferricyanide | $2.1 \times 10^{-3}$ mol. |
| Solvent buffer* | 1 l |
| pH as A | |
| *Solvent buffer was | |
| Triton X (TX-100) | |
| (3% aqueous solution) | 30 g |
| sodium carbonate | 20 g |
| water | 1 l | pKa Measurements used the method of Albert and Serjeant ("The Determination of Ionization Constant", Chapman and Hall, 1971). The word Triton is a trademark.

Analytical results, yield, solution activity and pKa data are recorded in Table II.

TABLE II

| Coupler No. | REQUIRES C | H | N | FOUND C | H | N | Yield % | EtOAc λmax (nm) | HBW (nm) | pKa | log kc-α | log kc-a |
|---|---|---|---|---|---|---|---|---|---|---|---|---|
| 1 | 65.3 | 6.98 | 27.76 | 65.4 | 7.0 | 27.7 | 54 | 538 | 88 | 9.5 | 5.4 | — |
| 2 | +59.2 | 5.5 | 15.3 | 59.3 | 5.8 | 15.4 | 81 | 546 | 93 | 11.8 | 3.46 | — |
| 3 | 58.2 | 6.8 | 27.2 | 58.3 | 6.8 | 27.1 | 81 | 550 | 90 | >11.8 | 4.76 | — |
| 4 | *57.0 | 6.7 | 26.6 | 57.4 | 7.0 | 25.4 | 14 | 538 | 95 | >11.8 | 4.88 | — |
| 5 | *61.2 | 7.3 | 17.9 | 60.1 | 7.1 | 17.5 | 16 | 536 | 107 | 11.8 | 3.98 | 5.78 |
| 6 | 64.3 | 5.4 | 12.5 | 62.9 | 5.6 | 11.6 | 77 | 538 | 88 | 9.5 | 5.10 | — |
| 7 | *65.3 | 6.6 | 16.3 | 65.7 | 6.3 | 16.0 | 67 | 538 | 97 | >11.8 | 3.78 | — |
| 8 | +65.4 | 7.8 | 9.1 | 65.5 | 7.9 | 9.1 | 54 | 538 | 90 | >11.8 | 3.41 | — |
| 9 | ϴ53.4 | 4.7 | 13.3 | 53.2 | 5.2 | 13.8 | 61 | 547 | 90 | 10.8 | 4.16 | 5.29 |
| 10 | *56.5 | 4.4 | 17.6 | 56.6 | 4.8 | 17.3 | 16 | 543 | 89 | — | — | — |
| 11 | ϴ61.6 | 4.1 | 14.4 | 61.4 | 4.1 | 14.0 | 45 | 579 | 101 | 11.0 | 4.86 | 6.16 |
| 12 | — | — | — | — | — | — | — | 602 | 108 | — | — | — |

*Analysis for 0.25 M water of crystallization
+Analysis for 0.5 M water of crystallization
ϴAnalysis for 0.75 M water of crystallization

EXAMPLE 3

Coupler (8) of the formula:

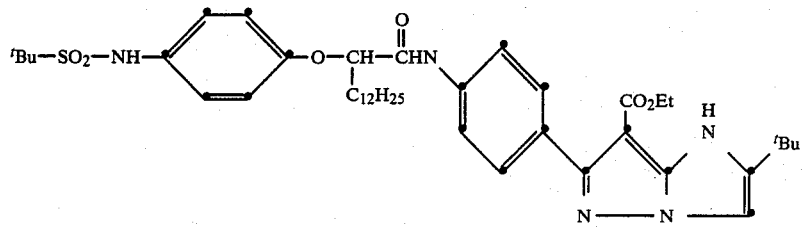

was dispersed in di-n-butyl phthalate (1:1 by weight) and coated in the following format:

| | |
|---|---|
| Gel | $1.07 \text{ g} \cdot \text{m}^{-2}$ |
| Bis-vinylsulphonyl-methyl ether (BVSME) | $0.008 \text{ g} \cdot \text{m}^{-2}$ |
| AgCl (undyed) | $0.538 \text{ g} \cdot \text{m}^{-2}$ |
| Antifoggant | $0.014 \text{ g} \cdot \text{m}^{-2}$ |
| Coupler | $0.69 \text{ m} \cdot \text{mole} \cdot \text{m}^{-2}$ (xg · m$^{-2}$) |
| di-n-butyl phthalate | xg · m$^{-2}$ |
| Gelatin | $3.225 \text{ g} \cdot \text{m}^{-2}$ |
| Poly(ethylene terephthalate) base | |

Check coatings of the known Coupler B instead of Coupler (8) in the same format were prepared for comparative purposes. This compound is typical of a pyrazolone coupler used in a photographic product.

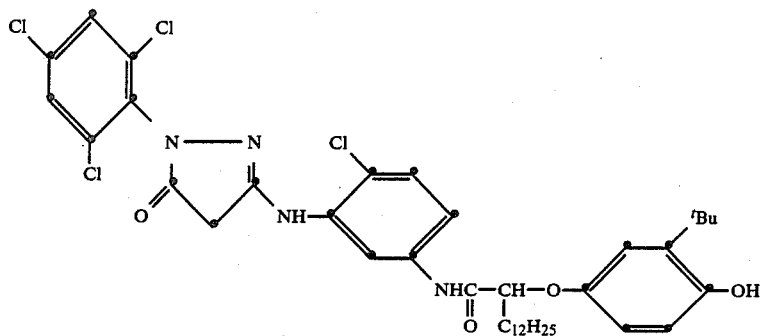

Coupler (B)

Exposed strips were processed to yield a good magenta dye image having an absorption maximum of 555 nm. Dye density measurements obtained from the process strips are given below:

|     | λmax | dye yield at λmax |
|-----|------|-------------------|
| (8) | 555  | 1.17              |
| (B) | 536  | 1.21              |

What is claimed is:

1. A photographic element comprising a support and a photographic silver halide emulsion having associated therewith a color coupler which comprises an imidazo[1,2-b]pyrazole nucleus and which reacts at its 3-position with an oxidized aromatic primary amino color developing agent and contains a non-coupling-off group in the 7-position.

2. A photographic element as in claim 1 wherein said color coupler has the general formula:

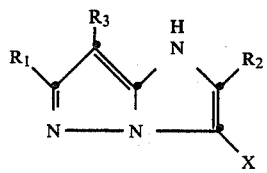

in which $R_1$ and $R_2$ are each hydrogen or a substituted or unsubstituted alkyl, a substituted or unsubstituted aryl, heterocyclic, hydroxy, nitrile, sulfone, acylamido, sulfonamido, sulfamoyl, alkoxycarbonyl, aryloxycarbonyl or nitro group, an amino or substituted amino group, a carbamoyl or substituted carbamoyl group, a non-coupling-off group alkoxy group or a non-coupling-off phenolic stabilizer moiety, $R_3$ is any of the non-coupling-off groups which $R_1$ and $R_2$ represent, and X is hydrogen or a group which splits off during coupling.

3. A photographic element as in claim 2 wherein X is a halogen, sulfo, carboxy, $R_4$—O—, $R_4$—S— wherein $R_4$ is a substituted or unsubstituted alkyl or aryl group or an amino or substituted amino group or an acyloxy, sulfonyloxy or benzotriazolyl group, or an azo radical rendering the coupler colored.

4. A photographic element as in claim 2 wherein the group X, when released from the coupler, forms a photographically useful compound.

5. A photographic element as in claim 2 wherein the group X, when released from the coupler, forms a photographically useful compound which is a development inhibitor.

6. A photographic element as in claim 2 wherein $R_1$, $R_2$ and $R_3$ represent a straight or branched chain alkyl group having 1–22 carbon atoms.

7. A process of forming a dye image in an exposed photographic element comprising a support and a photographic silver halide emulsion, said process comprising developing the photographic element with a silver halide color developing agent in the presence of a color coupler which comprises an imidazo-[1,2-b]pyrazole nucleus and which reacts at its 3-position with an oxidized aromatic primary amino color developing agent and said coupler contains a non-coupling-off group in the 7-position.

8. A process as in claim 7 wherein the color developing agent is a p-phenylenediamine.

9. A photographic element comprising a support and a photographic silver halide emulsion having associated therewith a color coupler selected from the group consisting of:

| Coupler No. | X | R1 | R2 | R3 |
|---|---|---|---|---|
| 1 | —H | ⟨benzene⟩—NO$_2$ | —t-Bu | —CO$_2$Et |
| 2 | —H | —H | —t-Bu | —CN |
| 3 | —H | —H | —t-Bu | —CONH$_2$ |
| 4 | —H | —H | —t-Bu | —CO$_2$Et |
| 5 | —OPh | ⟨benzene⟩—NO$_2$ | —t-Bu | —CO$_2$Et |

* * * * *